United States Patent [19]
Heckele

[11] Patent Number: 5,170,774
[45] Date of Patent: Dec. 15, 1992

[54] ENDOSCOPE WITH VIEWABLE AND TARGETABLE IRRIGATION AND ASPIRATION SYSTEM

[75] Inventor: Helmut Heckele, Knittlingen, Fed. Rep. of Germany

[73] Assignee: Richard Wolf GmbH, Knittlingen, Fed. Rep. of Germany

[21] Appl. No.: 670,849

[22] Filed: Mar. 18, 1991

[30] Foreign Application Priority Data

Mar. 17, 1990 [DE] Fed. Rep. of Germany ... 9003140[U]

[51] Int. Cl.$^5$ ............................................... A61B 1/00
[52] U.S. Cl. ...................................................... 128/4
[58] Field of Search ........................................ 128/4, 6

[56] References Cited

U.S. PATENT DOCUMENTS

| | | | |
|---|---|---|---|
| 3,850,162 | 11/1974 | Iglesias | 128/6 |
| 4,408,598 | 10/1983 | Ueda | 128/4 |
| 4,517,962 | 5/1985 | Heckele | 128/6 |
| 4,756,309 | 7/1988 | Sachse et al. | 128/6 |
| 4,881,523 | 11/1989 | Heckele | 128/4 |
| 4,924,851 | 5/1990 | Ognier et al. | 128/4 |
| 4,979,497 | 12/1990 | Matsura et al. | 128/4 |

FOREIGN PATENT DOCUMENTS

3923851  8/1990  Fed. Rep. of Germany .......... 128/6

Primary Examiner—Gene Mancene
Assistant Examiner—Todd E. Manahan
Attorney, Agent, or Firm—Cohen, Pontani, Lieberman, Pavane

[57] ABSTRACT

An endoscope provides for the examination of, and fluid delivery to, an operating field located in, for example, paranasal sinuses or the anterior base of the skull, for pressurized delivery of fluid and removal of tissue at a visually identified location. The endoscope includes a tubular shaft having a forward end for viewing the operating field, an optical viewer in connection with the shaft for providing a view of the operating field along an optical-exit axis, and irrigation and aspiration channels placed in connection with the shaft for providing targetted delivery of at least one jet of fluid at a location within the operating field along a fluid-delivery axis which intersects with the optical-exit axis at a distance from the forward end of the shaft, thereby enabling visual confirmation that the jet of fluid has impacted the targetted location simultaneously with the impact.

2 Claims, 1 Drawing Sheet

ENDOSCOPE WITH VIEWABLE AND TARGETABLE IRRIGATION AND ASPIRATION SYSTEM

FIELD OF THE INVENTION

The present invention relates to a surgical device preferably for use in nasal surgery, and more specifically to an endoscope with fluid delivery, guidance and aspiration means, having a tubular shaft, preferably with an oval cross section, through which are positioned an optical system with a lateral viewer and washing and suction delivery channels to facilitate observable and directionable irrigation, washing and suction for flushing out tissue, secretions, and the like.

BACKGROUND OF THE INVENTION

Endoscopes are known in the art for, inter alia, providing lighting and lens systems for visual examination of the interior of a body organ or cavity. Such devices are also used in otolaryngology, and allow viewing of the nasal passages, paranasal sinuses, base of the skull and the like while simultaneously providing for delivery of pressurized fluids for flushing and removal of nasal tissue, as well as secretions and discharge. An unobstructed view of the deep cavities which can be brought about by the pressurized-washing of occluding tissues, is as important as a precise surgical technique. Reference may be had in this regard to Federal Republic of Germany Patent 3803212, the text and teachings of which are hereby incorporated by reference as if set forth completely and at length, herein.

However, such devices do not allow the aiming of the fluidized discharge within the focal plane or focused field of view of the endoscope. Such a modified endoscopic instrument would improve many nasal surgical applications and treatments by allowing accurate targeting of the fluid followed by confirmation by simultaneous visualization that the fluid has impacted the target, including, e.g., for nasal polyps, tumors (including angiofibromas), mucocele or mucopyocele of the sinus, removal of nasal foreign bodies, as well as in treatment of sinusitis (ethmoidal, sphenoidal or frontal), folliculitis, and epistaxis.

Known surgical methods, like the Caldwell-Luc method for nasal polypectomy, require invasive surgical technique and are performed without tools to effectively enable the directionable washing or non-invasive removal of tissue, with visual confirmation and supervision made available to the surgeon. Likewise, cauterization to control bleeding in, e.g., Kiesslbach's area is often preceeded by the dispensation of a mild vasoconstrictor (e.g., phenylephrine), typically via a soaked cotton pressure pack, which generally dispenses the drug to a region, without simple ability to determine whether the target has successfully been reached.

Accordingly, it is an object of the present invention to provide an endoscope capable of visualization and targeting of, among other things, an otolaryngological site, followed by washing and removal of tissue (coagulated or otherwise) and, if necessary, application of other fluidized materials like, e.g., pharmaceuticals (including, e.g., phenylephrine followed by silver nitrate, chromic acid bead or other cauterization drugs).

It is yet another object of the present invention to provide a device for washing and suction while providing simultaneous observation of tissue through an optical system, and the loosening and/or removal of tissue, secretions or encrustations for use in nasal surgery.

It is still a further object of the present invention to provide the targeting of key otolarynogological areas and the presentation of fluids at the targeted areas with visual confirmation that the areas have been hit, and that the objective (e.g., removal of tissue, presentation of drugs, etc.) has been achieved without the need to resort to more invasive surgical techniques.

It is a yet further object of the present invention to provide a means and method for viewing deep cavities by stripping away view-occluding tissues through pressurized-fluid jetted at the location, followed by aspiration or other suction, all performed while simultaneously viewing the targetted operation site.

SUMMARY OF THE INVENTION

The foregoing objects, and other objects of the instant invention are achieved by the provision of an endoscope for the examination of, and fluid delivery to an operating field located in, for example, paranasal sinuses or the anterior base of the skull, for pressurized delivery of fluid and removal of tissue at a visually identified location. The endoscope, under a preferred embodiment of the instant invention, comprises a tubular shaft having a forward end for viewing the operating field, an optical viewer in connection with the shaft for providing a view of the operating field along an optical-exit axis, and irrigation and aspiration channels integrally placed in the shaft for providing targetted delivery of fluid at a location within the operating field along a fluid-delivery axis which intersects with the optical-exit axis at a distance from the forward end of the shaft, thereby enabling visual confirmation that the fluid has impacted the targetted location.

It is thus a primary feature of the instant invention to wash a region of surgical operation and draw off the wash liquid together with possible tissue parts, secretions or the like, thereby loosening, releasing and/or removing tissue parts and encrustations or the like present in the field of operation by directed, pressurized fluid delivery, while providing visual, simultaneous confirmation that the target has been hit.

BRIEF DESCRIPTION OF THE DRAWINGS

Other objects and many of the attendant advantages and features of the present invention will be readily appreciated and better understood by reference to, and consideration of the detailed description of the invention together with the accompanying drawings wherein like reference numerals designate like parts throughout the figures thereof, and wherein.

DETAILED DESCRIPTION OF THE INVENTION

Figure 1:
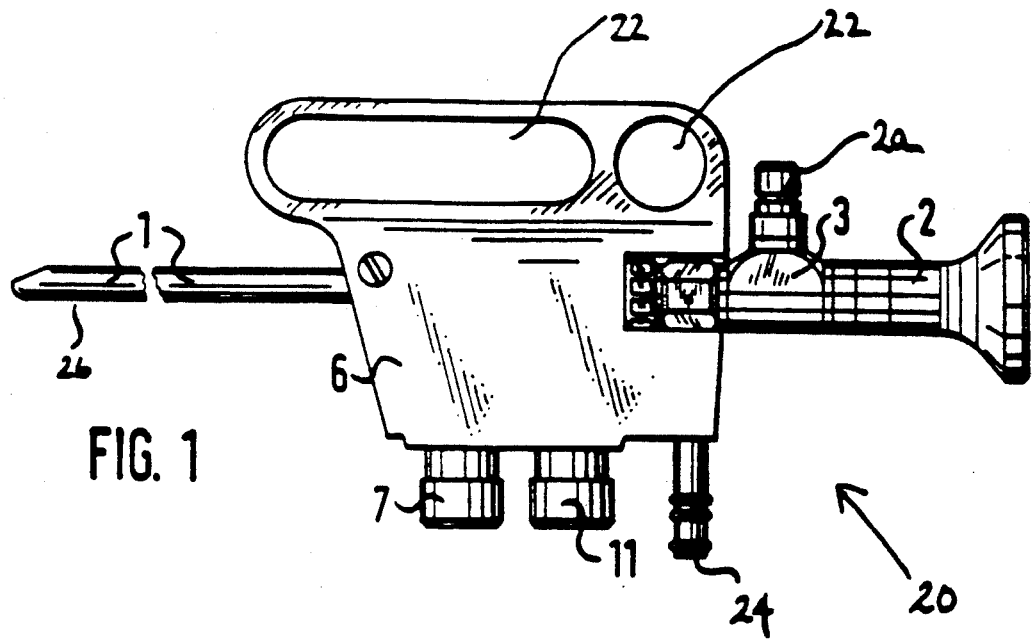
FIG. 1 is a side-view of the preferred embodiment of the endoscope of the instant invention.

In FIG. 1, an endoscope 20 is shown in accordance with a preferred embodiment of the instant invention, preferably for nasal surgery of the paranasal sinuses or the anterior base of the skull. Endoscope 20 is shown with a shaft 1 having a forward portion 26, a handle 6, an optical system 3, and an eyepiece 2 for viewing a targetted sight in an operating field. The optical system 3 comprises one of a number of different arrangements, e.g., mirrors and lenses, to provide for viewing through occular 2 and the provision of a light source through light guide connection 2a.

Handle 6 is shown in FIG. 1 in an optimized design based on ergonomic principles that benefit the user by placing the device simply and comfortably in the palm of the user's hand. Thus, a multiplicity of specially-configured finger grips 22 are provided in handle 6 for easy gripping, and access to valves 7 and 11, which are described in greater detail, below.

Figure 2:
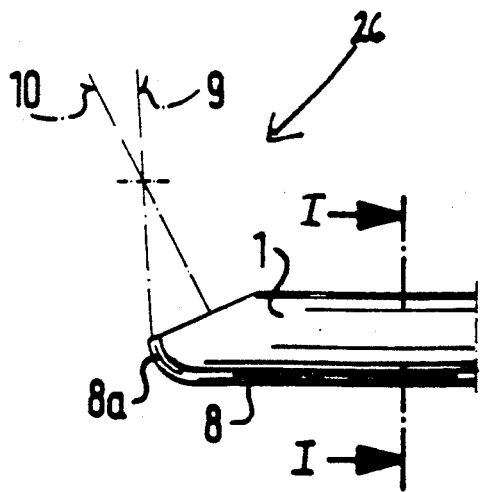
FIG. 2 is an enlarged side-view of the frontal portion of the preferred embodiment of the endoscope shown in FIG. 1, showing the angle of viewing and fluid dispensation, and the point of overlap.
Figure 3:
FIG. 3 is a cross-sectional view of the frontal portion of the endoscope along line I—I shown in FIG. 2.

FIG. 2 shows an enlarged view of the frontal portion 26 of shaft 1. FIG. 3 shows a cross-sectional view along line I—I of FIG. 2 of the frontal portion 26 of shaft 1. Optical system 3 is positioned to view an operating location placed within its focal plane, and along the optical-exit axis 10 which extends at an angle relative to the shaft 1 to enable lateral viewing. The shaft 1 is oval in cross-section, as shown in FIG. 3 to provide for a multiplicity of chambers running coaxially. Thus, a wash channel 4 and a suction channel 5 are created in the shaft by an optical system 3 running the length of the shaft. The channels 4, 5 are connected via handle 6 with valves 7 and 11, to a source of liquid and to vacuum or a collecting receiver, respectively, via conduit 24. It is understood that conduit 24 may itself be coaxial, may have two separate lines, or may reverse the flow to allow for aspiration and pressurized fluid dispensation, subject to the user's needs and controlled by valves 7 and 11, which may themselves be valves of a spring-loaded or push button type engageable by the user. Thus, the jet of pressure washing liquid may be delivered by any one of a number of means without departing from the scope of this invention, including actuating one or more of the valves 7 or 11 on the handle 6 or by means of a foot switch.

In accordance with the instant invention, beyond channels 4 and 5, an additional pressure washing channel 8 is provided which is connected to a source of liquid under pressure and extends laterally on the outside of the shaft 1, as shown in FIGS. 2 and 3. It is understood that extra channel 8, however, can also be provided inside the shaft 1. A distal end 8a of channel 8 is shown specially curved in FIG. 2 so that the fluid-exit axis 9 caused by fluid jetted out of the curvature 8a intersects the optical-exit axis 10 of the optical system 3 within the operating field, and, especially, within the focal point or focal field of the optical system 3. Thus, the wash jet escaping from distal end 8a strikes the center of the operating field within the visual view of the user, as he looks through the occular 2, and in this way tissue parts, encrustations or the like can be better loosened, since targetting can occur, and visual confirmation that the target has been hit.

In order to increase the effect of the jet of pressure washing liquid jetted out of end 8a, the pressure acting on the washing liquid can be increased, the cross-section of the nozzle can be reduced, or the jet of pressure washing liquid can be delivered in a pulsating manner.

Accordingly, while there have been shown, described and pointed out the fundamental novel features of the invention as applied to preferred embodiments thereof, it will be understood that various omissions, substitutions and changes in the form and details of the devices illustrated and in its operation and method may be made by those skilled in the art without departing from the spirit of the invention. It is the intention, therefore, to be limited only as indicated by the scope of the claims appended hereto.

I claim:

1. An endoscope for the examination of, and fluid delivery to a location, comprising:
    a tubular member having a forward end for placement proximate to said location;
    optical means positioned in connection with said tubular member for providing a focused field of view of said location, said optical means defining an optical-exit axis extending at an angle relative to the axis of the tubular member for lateral viewing of said location;
    irrigation and aspiration means integrally placed in connection with said tubular member for providing at least one jet of fluid at a target and suction for drawing off said fluid; and
    at least one pressure washing liquid channel for delivering a jet of washing liquid along a fluid-delivery axis, wherein said optical-exit axis intersects said fluid-delivery axis at a distance from the forward end of said tubular member.

2. The endoscope according to claim 1, wherein said tubular member has an oval cross-section.

* * * * *